(12) United States Patent
Van Driel et al.

(10) Patent No.: US 6,529,751 B1
(45) Date of Patent: Mar. 4, 2003

(54) OPTICAL DETECTION AND QUANTIFICATION OF MICROAIR IN BLOOD

(75) Inventors: Michael R. Van Driel, Fountain Valley, CA (US); Juan Carlos Flores, Huntington Beach, CA (US); Aaron S. Ingle, Laguna Beach, CA (US); Jorge Jeffery, Pasadena, CA (US); Craig R. Meyer, Simi Valley, CA (US); Yu-Tung Wong, Huntington Beach, CA (US); David L. Zollinger, Durham, NC (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/246,342

(22) Filed: Feb. 8, 1999

Related U.S. Application Data

(63) Continuation of application No. 08/841,015, filed on Apr. 29, 1997, now abandoned.

(51) Int. Cl.$^7$ ................................................. A61B 5/00
(52) U.S. Cl. ........................ 600/322; 604/67; 604/122; 250/573; 340/619
(58) Field of Search ................................. 600/310, 322; 604/65, 67, 122, 123; 250/338.1, 343, 573, 574, 575, 576; 340/619, 632, 627; 73/861.41

(56) References Cited

U.S. PATENT DOCUMENTS

| | | |
|---|---|---|
| 3,812,482 A | 5/1974 | Clark ............................ 340/237 |
| 3,989,625 A | 11/1976 | Mason ........................... 210/94 |
| 3,990,444 A | 11/1976 | Vial |
| 4,122,713 A | 10/1978 | Stasz et al. .................... 73/194 |
| 4,181,610 A | 1/1980 | Shintani et al. ................ 210/85 |
| 4,280,495 A | 7/1981 | Lampert |
| 4,367,736 A | 1/1983 | Gupton |
| 4,496,346 A * | 1/1985 | Mosteller ...................... 604/122 |
| 4,658,244 A | 4/1987 | Meijer .......................... 340/632 |
| 4,784,643 A | 11/1988 | Siretchi et al. .............. 604/122 |
| 4,797,655 A * | 1/1989 | Orndal et al. ................... 604/67 |
| 5,103,214 A | 4/1992 | Curran et al. ................ 340/691 |
| 5,533,512 A | 7/1996 | Novotny et al. |
| 5,644,402 A | 7/1997 | Chevallet ...................... 356/440 |
| 5,672,887 A | 9/1997 | Shaw et al. .................. 250/573 |
| 5,680,111 A * | 10/1997 | Danby et al. ................. 250/573 |

FOREIGN PATENT DOCUMENTS

| | | |
|---|---|---|
| EP | 0 467 805 | 3/1995 |
| EP | 0 704 044 | 12/1999 |

* cited by examiner

*Primary Examiner*—Eric F. Winakur
(74) *Attorney, Agent, or Firm*—Stout, Uxa, Buyan & Mullins, LLP; Donald E. Stout

(57) ABSTRACT

Both the number and the size of microair bubbles in a bloodstream are accurately determined optically, independently of oxygen saturation, by monitoring the intensity of light transmission in the 800–850 nm range through the bloodstream and indicating the count and amplitude range of peaks in the monitored intensity.

5 Claims, 3 Drawing Sheets

OPTICAL DETECTION AND QUANTIFICATION OF MICROAIR IN BLOOD

This application is a continuation, of application Ser. No. 08/841,015, filed Apr. 29, 1997, now abandoned.

FIELD OF THE INVENTION

This invention relates to the detection and quantification of microair in blood, and more particularly to an infrared system for counting microair bubbles in a bloodstream and determining their size.

BACKGROUND OF THE INVENTION

During open-heart surgery, microscopic air bubbles having a diameter on the order of 60–300 μm are frequently entrained into the blood circuit of the heart-lung machine in spite of careful defoaming of the blood passing through the machine. These microair bubbles have been suspected of causing strokes, memory loss and other undesirable effects in the patient. It is therefore important in a heart-lung machine to detect the presence and size of these bubbles remaining in the bloodstream after filtration so that their origin can be traced and appropriate remedial measures can be taken when the presence of microair is detected in the blood circuit.

Microair detection in the prior art has conventionally been done by transmitting an ultrasound beam through a bloodstream flowing past the detector. The problem with this approach is that ultrasound is expensive and is neither able to accurately evaluate the size of individual bubbles, nor detect them as individual bubbles when they are close together. Also, ultrasound measures discontinuities in the bloodstream and therefore cannot distinguish between microair and tiny blood clots. Also, the accuracy of ultrasound measurements becomes poor for very small diameter bubbles. Furthermore, in pulsing ultrasound applications, the propagation velocity of sound required ultrasound pulses to be at least 10–20 μsec apart for a fast-moving 1.25 cm diameter bloodstream, so that tracking is not continuous. Consequently, a more accurate and discriminating method of detecting microair was needed.

Prior to the present invention, optical detection of microair was of limited use because it only operated in a binary (bubble present or absent) mode. Quantitative detection was considered impractical because light transmission through a bloodstream is strongly affected by hematocrit and oxygen saturation, which vary unpredictably during surgery.

SUMMARY OF THE INVENTION

The present invention allows highly accurate detection and measurement of microair over a wide range of bubble sizes by detecting the translucence of a bloodstream to infrared radiation having a wavelength of about 800–850 nm in at least two directions at a substantial angle to each other. The detection is made by detecting spikes in the amplitude of infrared signals received by an array of infrared sensors disposed around a column of blood when microair bubbles pass the field of view of the sensors.

DESCRIPTION OF THE PREFERRED EMBODIMENT

Figure 1:
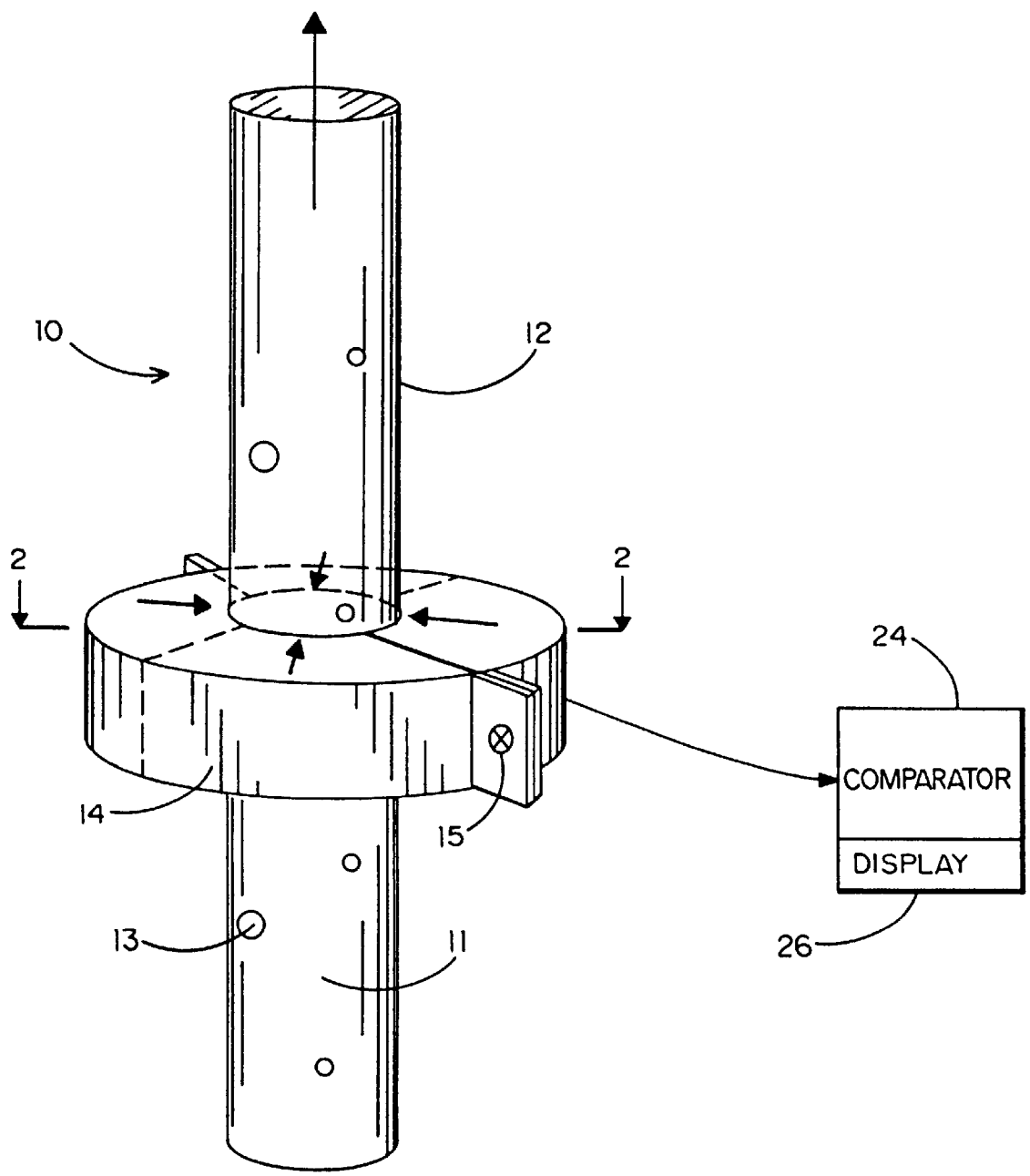
FIG. 1 is a perspective view of a microair detector according to the invention.
Figure 2:
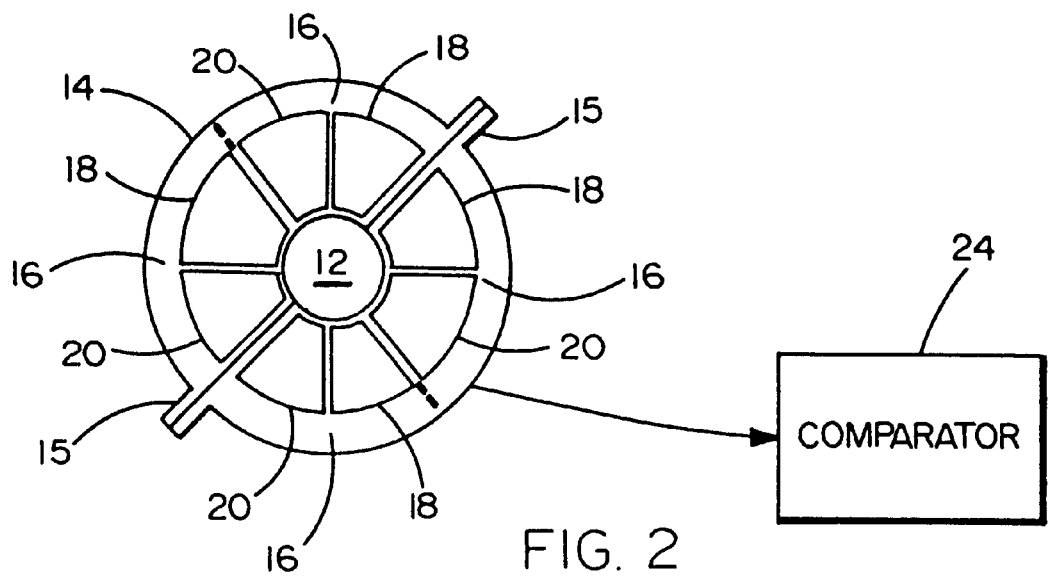
FIG. 2 is a section along line 2—2 of FIG. 1.
Figure 3:
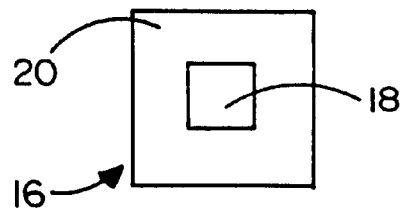
FIG. 3 is a front view of an infrared emitter/receiver useful in the invention.

FIGS. 1–3 show an optical microair detector system 10 according to the invention. Blood 11 containing microair bubbles 13 flows through a rigid, transparent tube 12 preferably formed of polycarbonate. Rigidity of the tube 12 is necessary because the pulsations of the blood flow in a heart-lung machine expand and contract the walls of a flexible tube enough to create a rhythmic noise in the detector and degrade the signal quality.

Disposed around the tube 12 in a light-tight enclosure 14 clamped around the tube 12 by fasteners 15 are two or more opposed sets 16 of combination light sources 18 and photodetectors 20. The light source 18 and photodetector 20 of each set 16 may be nested within each other as shown in FIG. 2, or disposed side by side as shown in FIG. 3. The light sources 18 illuminate the opposing detectors 20 through the blood in the tube 12. The number of sets 16 will depend upon the diameter of the tube 12 and the dimensions of the sets 16, but they are preferably so disposed (FIG. 3) that the entire cross section of the tube 12 is either directly in the light path of a set 16, or at least is substantially illuminated by the side scatter of a light beam from a set 16.

In the above-described apparatus, the detection of intensity changes in light signals passed through the tube 12 is the key to detecting the presence of a bubble 13. These changes in the light intensity can be caused either by highly obstructing particles (clots, bone chips, etc.) or by air emboli or bubbles 13 that reflect light at their surfaces and allow the remaining light to pass through without the absorptive effects of blood. It is possible to determine what kind of obstruction has passed through the detector, as well as the size of that obstruction, by tracking the resulting variations in the light signal impinging upon the photodetectors 20.

The variations in the impinging light intensity caused by bubbles 13 are due to the difference between the optical properties of the blood 11 and the bubbles 13. Light travelling through the blood 11 is both scattered and absorbed by the different component particles of blood, such as red blood cells, water molecules, and platelets. Light is absorbed both by the hemoglobin found in red blood cells and the water molecules. Scattering, where the light is deflected by some angle, generally results when the light interacts either with red blood cell bodies or phospholipids.

In very simple (non-blood) media where scattering is negligible and absorption is the primary effect, Beer's law can be used to model the light intensity as it passes through the medium:

$$I(x) = I_o e^{-\mu_a x}$$

where $I(x)$ is the intensity of the transmitted light at a distance x travelled through the medium, $I_o$ is the incident light intensity, and $\mu_a$ is the absorption coefficient.

Figure 4:
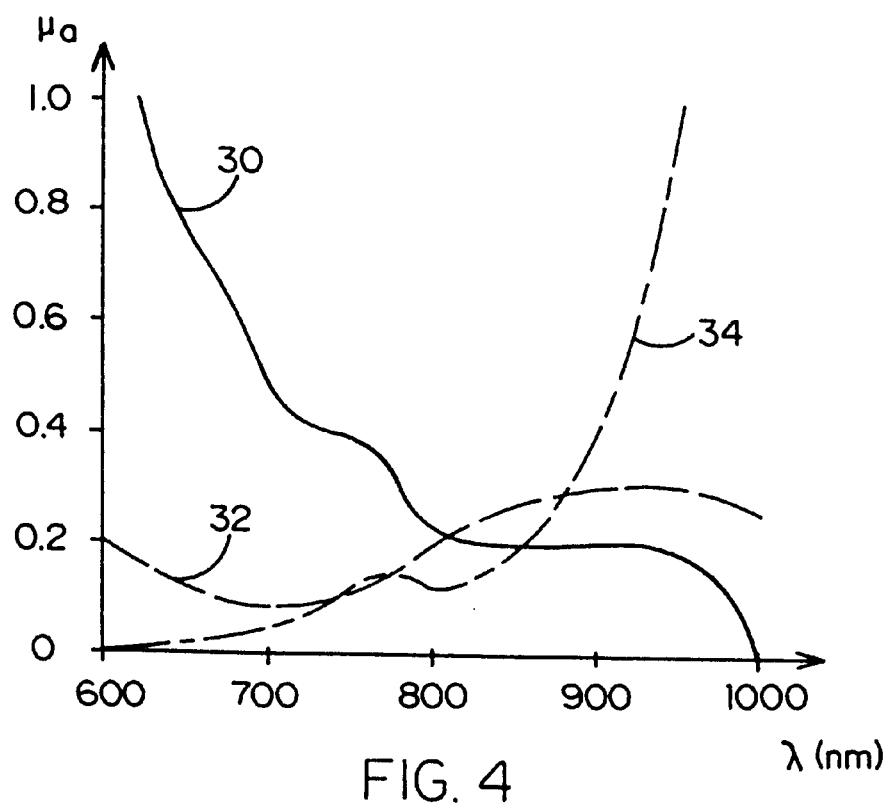
FIG. 4 is a wavelength-absorption diagram showing the light absorption coefficients of various media as a function of wavelength.

However, the situation in the blood 11 is not so simple. In blood, the scattering effect cannot be neglected, and in fact, is a much larger factor than absorption. The absorption coefficient ($\mu_a$) for light in blood at a wavelength of 800 nm is approximately 1 cm$^{-1}$. This value is the inverse of the mean free path (the mean distance travelled by the individual photons through the blood medium before absorption). This number is highly dependent on several factors, including the oxygen saturation of the blood, the hematocrit (% by volume of red blood cells), and the wavelength of light used. FIG. 4 shows the three major blood components and their absorption coefficients' dependence upon wavelength. In FIG. 4, curve 30 denotes de-oxyhemoglobin, curve 32 denotes oxyhemoglobin, and curve 34 denotes water. The values for oxygen saturation (fraction of oxyhemoglobin to total hemoglobin) and hematocrit may change over the course of the surgery, which may in turn cause variation of the absorption of the blood as the relative concentrations of the three absorbing components in FIG. 4 change. Because slight concentration changes cause large changes in absorption in certain parts of the spectrum (e.g. 900–1000 nm), the invention uses a wavelength in the 800–850 nm range, where the de-oxyhemoglobin is level (i.e. the dependency on oxygen saturation is eliminated) and the water absorption is minimized.

The scattering coefficient ($\mu_s$) for light in blood is approximately 300 cm$^{-1}$ assuming $\mu_s = \Sigma$ (fraction of component) ($\mu_s$ of each component) for components such as water, platelets, red blood cells with oxy-hemoglobin and de-oxyhemoglobin, etc. This coefficient describes all scattering occurrences, including both forward and backscattering. Another factor, g, is introduced to describe the mean cosine of the scattering angle during scattering events. The effective scattering $\mu'_s = \mu_s (1g)$ is a measure of the degree to which large angle scattering events occur in the medium.

In, blood g$\approx$0.974 so $\mu'_s \approx 8$ cm$^{-1}$, still much higher than the $\mu_a \approx 1$ cm$^{-1}$.

The apparatus of this invention can distinguish between microair bubbles 13 and small particulates such as blood clots and bone chips. Because of their increased absorption over blood, the light intensity drops significantly behind these particles, forming an effective shadow, instead of the increase in intensity due to a bubble. This makes particulates and bubbles easy to distinguish.

Figure 5:
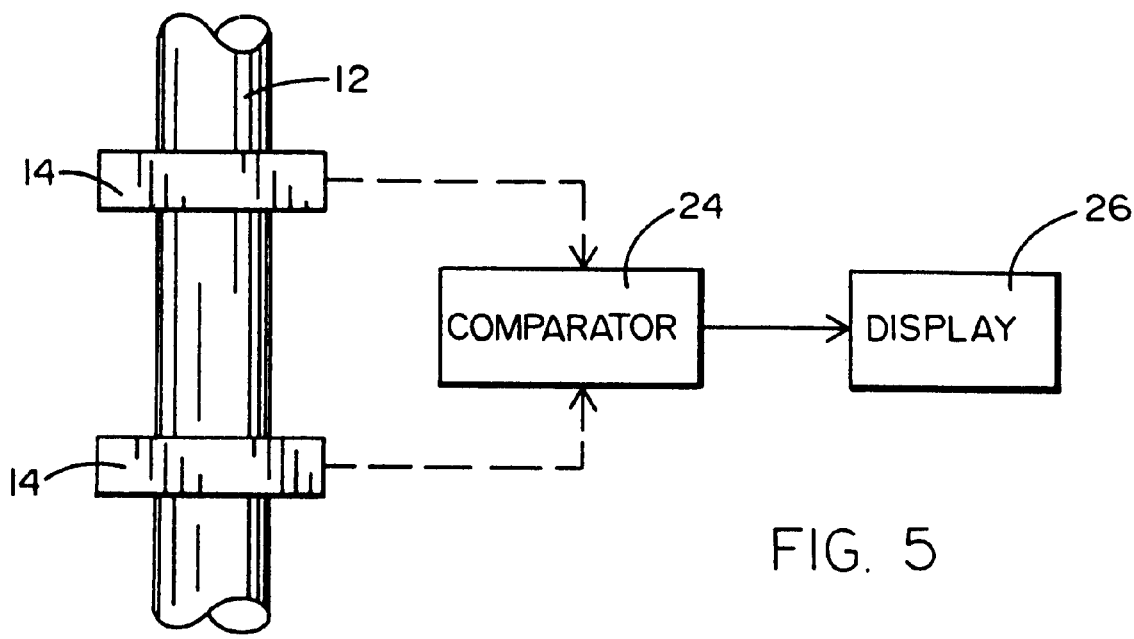
FIG. 5 illustrates an alternative embodiment of the invention.

In order to increase the accuracy of the bubble size determination, it is advantageous to use a plurality of axially spaced detector sets 16 (FIG. 5), or to use CCD arrays which can track individual bubbles as they move through the detector's field of vision. Because bubbles rise within the bloodstream at a rate generally proportional to their size, a time correlation can be obtained by observing the intensity signal at spaced points along the tube 12. This time correlation in turn can be used to check and increase the accuracy of the optical bubble measurement.

Figure 6:
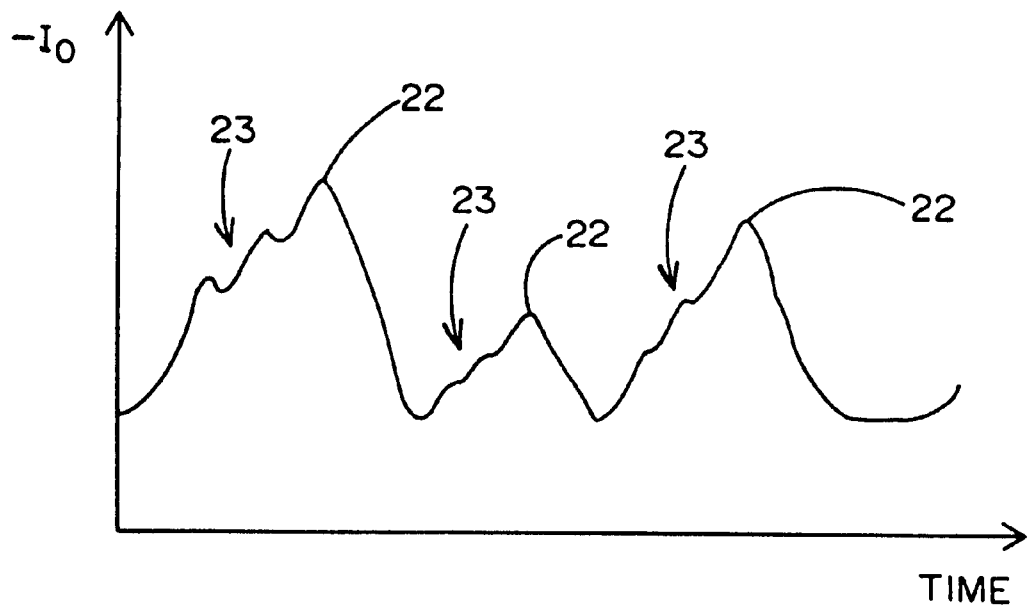
FIG. 6 is a time-amplitude diagram showing the amplitude pattern produced by the passage of microair bubbles through the detector.

FIG. 6 shows the effect 22 of the passage of bubbles 13 of different sizes past the detector 10 of FIG. 1 (the more negative the output voltage in FIG. 6, the more light has passed through the blood 11). By measuring the amplitude (and, in the embodiment of FIG. 5, the timing) of the peaks 22, and the relation of artifacts 23 to the peaks 22, a conventional comparator 24 can provide an indication, to a numerical display 26, of the count of bubbles 13 in various size ranges.

It is understood that the exemplary optical detection and quantification of microair in blood described herein and shown in the drawings represents only a presently preferred embodiment of the invention. Indeed, various modifications and additions may be made to such embodiment without departing from the spirit and scope of the invention. Thus, other modifications and additions may be obvious to those skilled in the art and may be implemented to adapt the present invention for use in a variety of different applications.

What is claimed is:

1. An optical detector for detecting and measuring microair bubbles in a bloodstream, comprising:
    a) a rigid transparent conduit for said bloodstream;
    b) at least one light source positioned adjacent said conduit, said light source transmitting light having a wavelength substantially in the range of 800–850 nm through said conduit;
    c) at least one light receiver positioned adjacent said conduit opposite said light source, said light receiver producing a signal representative of the light intensity impinging upon said receiver;
    d) an apparatus operatively connected to said receiver to provide an indication, as a function of said signal, of the number and size of microair bubbles passing said detector.

2. The detector of claim 1, in which said apparatus includes a comparison device arranged to detect the occurrence and amplitude range of peaks in said signal.

3. The detector of claim 1, in which said at least one light source and said at least one receiver are disposed in at least one opposing pair, each pair having a light source and a receiver.

4. The detector of claim 3, in which sufficient pairs are disposed around said conduit to illuminate substantially all of the cross-sectional area of said conduit.

5. The detector of claim 1, in which a plurality of detectors spaced from one another in a direction axial of said conduit are disposed about said conduit.

* * * * *